(12) United States Patent
Yotani et al.

(10) Patent No.: US 9,447,460 B2
(45) Date of Patent: Sep. 20, 2016

(54) METHOD FOR DETECTING SINGLE NUCLEOTIDE POLYMORPHISMS

(71) Applicant: SEKISUI MEDICAL CO., LTD., Tokyo (JP)

(72) Inventors: Takuya Yotani, Ibaraki (JP); Eiji Kiyotoh, Ibaraki (JP); Koji Ushizawa, Tokyo (JP)

(73) Assignee: Sekisui Medical Co., Ltd., Tokyo (JP)

( * ) Notice: Subject to any disclaimer, the term of this patent is extended or adjusted under 35 U.S.C. 154(b) by 0 days.

(21) Appl. No.: 14/669,735

(22) Filed: Mar. 26, 2015

(65) Prior Publication Data
US 2015/0197795 A1  Jul. 16, 2015

Related U.S. Application Data

(63) Continuation of application No. 13/979,256, filed as application No. PCT/JP2012/050430 on Jan. 12, 2012, now abandoned.

(30) Foreign Application Priority Data

Jan. 12, 2011  (JP) .................................. 2011-004216
Mar. 31, 2011  (JP) .................................. 2011-080369

(51) Int. Cl.
*C12Q 1/68* (2006.01)
*C07H 21/00* (2006.01)

(52) U.S. Cl.
CPC ........... *C12Q 1/6844* (2013.01); *C12Q 1/6858* (2013.01)

(58) Field of Classification Search
CPC .......................... C12Q 1/6844; C12Q 1/6858
USPC .......................................... 435/6.1; 536/25.4
See application file for complete search history.

(56) References Cited

U.S. PATENT DOCUMENTS

| | | | |
|---|---|---|---|
| 4,704,274 A | 11/1987 | Sakuma et al. | |
| 5,438,128 A | 8/1995 | Nieuwkerk et al. | |
| 2002/0197629 A1 | 12/2002 | Gjerde et al. | |
| 2007/0154892 A1 | 7/2007 | Wain-Hobson et al. | |
| 2008/0076910 A1 | 3/2008 | Takkellapati et al. | |
| 2009/0053719 A1* | 2/2009 | Lo ........................ | C12Q 1/6851 435/6.11 |
| 2013/0330735 A1 | 12/2013 | Yotani et al. | |
| 2014/0349284 A1 | 11/2014 | Yotani et al. | |

FOREIGN PATENT DOCUMENTS

CN   1451762   10/2003
CN   1880480   12/2006
(Continued)

OTHER PUBLICATIONS

Randall K. Saiki et al.; "Analysis of enzymatically amplified β-globin and HLA-DQa DNA with allele-specific oligonucleotide probes"; Nature; vol. 324; Nov. 1986; pp. 163-166.
(Continued)

*Primary Examiner* — Jezia Riley
(74) *Attorney, Agent, or Firm* — Wenderoth, Lind & Ponack, L.L.P.

(57) ABSTRACT

An object of the present invention is to provide a method for rapidly and simply detecting single nucleotide polymorphisms. The present invention is a method for detecting single nucleotide polymorphisms, comprising analyzing wild-type and mutant-type products amplified by an AS-PCR method using ion-exchange chromatography.

2 Claims, 3 Drawing Sheets

(56) References Cited

FOREIGN PATENT DOCUMENTS

| | | |
|---|---|---|
| CN | 101323852 | 12/2008 |
| CN | 101899437 | 12/2010 |
| CN | 101899511 | 12/2010 |
| DE | 697 29 182 | 1/2005 |
| EP | 2 366 719 | 9/2011 |
| EP | 2692863 | 2/2014 |
| JP | 5-99909 | 4/1993 |
| JP | 2002-187897 | 7/2002 |
| JP | 2004-513625 | 5/2004 |
| JP | 2004-514874 | 5/2004 |
| JP | 2004-180637 | 7/2004 |
| JP | 2005-027518 | 2/2005 |
| JP | 2005-323565 | 11/2005 |
| JP | 2006-075126 | 3/2006 |
| JP | 2009-524412 | 7/2009 |
| JP | 2010-504738 | 2/2010 |
| WO | 97/29825 | 8/1997 |
| WO | 01/27331 | 4/2001 |
| WO | 2007/091125 | 8/2007 |
| WO | 2008/039664 | 4/2008 |
| WO | 2008/039668 | 4/2008 |

OTHER PUBLICATIONS

Corresponding U.S. Appl. No. 14/008,770, filed Mar. 30, 2012.
D'Anna et al., "Histones H1o a and H1o b Are the Same as CHO Histones H1 (III) and H1(IV): New Features of H1o Phosphorylation during the Cell Cycle", Biochemistry, vol. 20, Jul. 21, 1981, pp. 4501-4505.
Ghrist et al., "Predicting Bandwidth in the High-Performance Liquid Chromatographic Separation of Large Biomolecules", Journal of Chromatography, vol. 387, 1987, pp. 1-19.
Iny et al., "Isolation of a thermophilic alkaline phosphatase by either hydrophobic or Procion red Sepharose chromatography", Journal of Chromatography, vol. 360, 1986, pp. 437-442.
Tsuchihashi et al., "Progress in high throughput SNP genotyping methods", The Pharmacogenomics Journal, vol. 2, No. 2, 2002, pp. 103-110.
Extended European Search Report issued Nov. 5, 2014 in European Patent Application No. 12734660.9.
Thayer, J.R. et al. "Control of oligonucleotide retention on a pH-stabilized strong anion exchange column", Analytical Biochemistry, Academic Press Inc., New York. vol. 338, No. 1, pp. 39-47, Mar. 1, 2005.
Gaudet, et al. "Allele specific PCR in SNP genotyping", Single Nucleotide Polymorphisms: Methods and Protocols, Humana Press, USA, pp. 415-423, Jan. 1, 2009.
Extended European Search Report issued Dec. 8, 2014 in counterpart European Patent Application No. 12734188.1.
Okimoto, R. et al., "Improved PCR Amplification of Multiple Specific Alleles (PAMSA) Using Internally Mismatched Primers", BioTechniques, vol. 21, pp. 20-26 (Jul. 1996).
Extended European Search Report issued Jan. 23, 2015 in counterpart European Patent Application No. 12765405.01.
Neitzel et al., "Easy, Accurate and Reliable Screening for SNPs by Ion Pair/Reverse Phase HPLC: Simultaneous Detection of Factor V G1691A, Prothrombin G20210A and Methylenetetrahydrofolate Reductase C677T Variants", Clinical Lab, vol. 49, pp. 313-318, 2003.
Seipp et al., "Quadruplex Genotyping of F5, F2, and MTHFR Variants in a Single Closed Tube by High-Resolution Amplicon Melting", Clinical Chemistry, vol. 54, No. 1, pp. 108-115, 2008.
Webster et al., "Analysis of variation in the human β-globin gene cluster using a novel DHPLC technique", Mutation Research, vol. 501, pp. 99-103, 2002.
International Search Report issued Apr. 17, 2012 in International (PCT) Application No. PCT/JP2012/050430.
Huang et al., "A Simple and Rapid Modified New Method for SNP Typing by Fragment Length Discrepant Allele Specific PCR", Journal of Forensic Medicine, vol. 21, No. 1, Feb. 2005, with English language Abstract.
Corresponding U.S. Appl. No. 13/979,241, filed Jan. 12, 2012.
Yoshio Kato et al., "Separation of DNA restriction fragments by high-performance ion-exchange chromatography on a nonporous ion exchanger", Journal of Chromatography, 1989, vol. 478, No. 1, pp. 264-268.

\* cited by examiner

SEQUENCE LISTING

<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 1
cgcctcgttg tacatcagag cgg                                    23

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: primer

<400> SEQUENCE: 2
ctgacgcctc gttgtacatc agagcga                                27

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 3
cacatcctcc ctttggaatg gca                                    23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: primer

<400> SEQUENCE: 4
gaaagggtcc gtcagcatga c                                      21

-continued

```
<210> SEQ ID NO 5
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 5
atagttgtcc tagcacctga cgcctcgttg tacatcagag cga                           43
```

METHOD FOR DETECTING SINGLE NUCLEOTIDE POLYMORPHISMS

This application is a Continuation of Ser. No. 13/979,256, filed Jul. 11, 2013, now Abandoned, which is a 371 U.S. national stage of International Application No. PCT/JP2012/050430 filed Jan. 12, 2012, herein incorporated by reference in their entirety.

TECHNICAL FIELD

The present invention relates to a method for rapidly and simply detecting single nucleotide polymorphisms.

BACKGROUND ART

In recent years, techniques have been developed for analyzing single nucleotide polymorphisms (SNP) which have been shown to be associated with various diseases and drug side effects; in the development thereof, it is an important factor to accurately detect single nucleotide polymorphisms simply and in a short time.

An RFLP (Restriction Fragment Length Polymorphism) method is known as a method for analyzing single nucleotide polymorphisms. The RFLP method involves, when a restriction enzyme exists recognizing a gene mutation site in a PCR (Polymerase Chain Reaction) amplification product, preparing primers in common sequence sites, performing amplification by holding polymorphisms in the PCR amplification product, cleaving the resultant PCR product with the restriction enzyme, and determining the presence of polymorphisms based on the length of the fragments. However, the method has problems including that the use of restriction enzyme increases analysis cost and prolongs time of the whole analysis. It also has problems including that the detection of the chain length difference by electrophoresis complicates operation and prolongs time of the whole analysis.

In the fields of biochemistry, medicine, and the like, ion-exchange chromatography is used for the separation of biomacromolecules such as nucleic acids, proteins, and polysaccharides as a method capable of accurately detecting them simply and in a short time. The use of ion-exchange chromatography reduces complicated operation as required for measurement by electrophoresis. Non Patent Literature 1 discloses a method for separating nucleic acid-related compounds by high-performance liquid chromatography. However, even the method disclosed in Non Patent Literature 1 has a problem that it is difficult to sufficiently separate nucleic acids having chain lengths approaching to each other such as single nucleotide polymorphisms.

CITATION LIST

Non Patent Literature

Non Patent Literature 1: "Raifusaiensu Notameno Kosoku Ekitai Kuromatogurafi Kiso To Jikken (High-Performance Liquid Chromatography for Life Science) (Basis and Experiment)", Hirokawa Shoten, pp. 333-359.

SUMMARY OF INVENTION

Technical Problem

An object of the present invention is to provide a method for rapidly and simply detecting single nucleotide polymorphisms.

Solution to Problem

The present invention is a method for detecting single nucleotide polymorphisms, comprising analyzing wild-type and mutant-type products amplified by an AS-PCR method using ion-exchange chromatography.

The present invention will be described below in detail.

The present inventors have found that the wild-type and mutant-type products amplified by an AS-PCR method can be analyzed using ion-exchange chromatography to detect single nucleotide polymorphisms rapidly and simply, thereby accomplishing the present invention.

The AS-PCR (Allele Specific-PCR) method is a method for detecting gene polymorphism (particularly, single nucleotide polymorphisms) using a sequence-specific amplification reaction. Specifically, PCR is performed in such a manner that a nucleotide sequence of a single nucleotide polymorphism desired to be detected is located at the 3' end of primer. When the sequence of the target nucleic acid is completely complementary to the primer, an extension reaction by DNA polymerase occurs. In contrast, when the sequence of the target nucleic acid is incompletely complementary to the primer, the extension reaction of DNA polymerase is inhibited. Thus, it is a method which involves using two primers, which have a wild-type or mutant-type nucleotide sequence of a single nucleotide polymorphism at the 3' end, to perform the determination of the single nucleotide polymorphism based on the results of the amplification reaction. The AS-PCR method can use a method as disclosed in "Nature, 324, p. 163-166, 1986".

The method for detecting single nucleotide polymorphisms according to the present invention uses ion-exchange chromatography.

The eluent used for ion-exchange chromatography preferably contains a guanidine salt derived from guanidine represented by formula (1) below.

[Chem. 1]

(1)

Examples of the guanidine salt include guanidine hydrochloride, guanidine sulfate, guanidine nitrate, guanidine carbonate, guanidine phosphate, guanidine thiocyanate, guanidine sulfamate, aminoguanidine hydrochloride, and aminoguanidine bicarbonate. Guanidine hydrochloride and guanidine sulfate are preferably used, among these.

The concentration of a guanidine salt in the eluent when analyzed may be properly adjusted in accordance with a substance to be detected; however, it is preferably 2,000 mmol/L or less.

Specifically, a method can be mentioned which involves performing gradient elution in the guanidine salt concentration range of 0 to 2,000 mmol/L. Thus, it is not necessary that the concentration of the guanidine salt in starting analysis is 0 mmol/L, and it is also not necessary that the concentration of the guanidine salt in terminating analysis is 2,000 mmol/L.

The method of gradient elution may be a low-pressure gradient method or a high-pressure gradient method; however, a method is preferable which involves carrying out elution while performing precise concentration adjustment by the high-pressure gradient method.

The guanidine salt may be added alone to the eluent or in combination with another salt. Examples of the salt capable of being used in combination with the guanidine salt include salts consisting of halides and alkali metals, such as sodium chloride, potassium chloride, sodium bromide, and potassium bromide, salts consisting of halides and alkali earth metals, such as calcium chloride, calcium bromide, magnesium chloride, and magnesium bromide, and inorganic acid salts such as sodium perchlorate, potassium perchlorate, sodium sulfate, potassium sulfate, ammonium sulfate, sodium nitrate, and potassium nitrate. Organic salts such as sodium acetate, potassium acetate, sodium succinate, and potassium succinate may also be used.

A known buffer or an organic solvent can be used as a buffer used in an eluent; specific examples thereof include Tris-hydrochloric acid buffer, TE buffer consisting of Tris and EDTA, TAE buffer consisting of Tris, acetic acid, and EDTA, and TBA buffer consisting of Tris, boric acid, and EDTA.

The pH of the eluent is not particularly limited, as long as it is in a range that allows the separation of nucleic acid chains by anionic exchange.

The filler used for ion-exchange chromatography is preferably one having cationic groups introduced into at least the surface of base material particles, and more preferably one having strong cationic groups and weak anionic groups on at least the surface of base material particles.

As used herein, the "strong cationic group" means a cationic group dissociating in the wide pH range of 1 to 14. Thus, the strong cationic group can retain a dissociated (cationized) state without being affected by the pH of the aqueous solution.

Examples of the strong cationic group include quaternary ammonium groups. Specific examples thereof include trialkylammonium groups such as a trimethylammonium group, a triethylammonium group, and a dimethylethylammonium group.

Examples of counter ions for the strong cationic group include halide ions such as chloride ion, bromide ion, and iodide ion.

The amount of the strong cationic group is not particularly limited; however, the lower limit thereof per dry weight of the filler is preferably 1 µeq/g and the upper limit is preferably 500 µeq/g. A strong cationic group amount of less than 1 µeq/g may weaken the retaining force of the filler and deteriorate separation performance. A strong cationic group amount of more than 500 µeq/g may pose problems of making the retaining force of the filler too strong, thereby not easily causing the elution of a substance, prolonging analysis time, and the like.

As used herein, the "weak anionic group" means an anionic group having a pKa of 3 or more. Thus, the weak anionic group described above is affected by the pH of the aqueous solution, by which the dissociated state thereof changes. A pH of more than 3 causes the dissociation of the proton of the carboxy group and increases the percentage thereof having a minus charge. Conversely, a pH of less than 3 increases the percentage of the carboxy group in an undissociated state in which the proton of the carboxy group is bonded.

Examples of the weak anionic group described above include a carboxy group and a phosphoric acid group. A carboxy group is preferable, among these.

Examples of methods for introducing carboxy groups into at least the surface of base material particles, which can be used, include known methods such as a method involving copolymerizing a monomer having a carboxy group, a method involving hydrolyzing the ester moiety of a monomer, a method involving forming a carboxy group by ozonated water treatment, a method involving forming a carboxy group using ozone gas, a method involving forming a carboxy group by plasma treatment, a method involving reacting a silane coupling agent having a carboxy group, and a method involving copolymerizing a monomer having an epoxy group and forming a carboxy group by ring-opening of the epoxy group. Among these, a method involving forming a carboxy group by ozonated water treatment is preferably used when the base material particle has hydrophobic structural portions, particularly carbon-carbon double bonds.

The method involving forming a carboxy group by ozonated water treatment will be described.

Ozone has high reactivity with a double bond, and the ozone reacting with the double bond forms ozonide as an intermediate, followed by the formation of a carboxy group and the like.

Ozonated water means what is formed by dissolving ozone gas in water.

Ozonated water can be used to simply oxidize the particle surface by merely dispersing the particles in the ozonated water. As a result, hydrophobic structural portions in the base material particle can be considered to be oxidized to form hydrophilic groups such as a carboxy group, a hydroxyl group, an aldehyde group, and a keto group.

Ozone has a strong oxidation effect; treatment with ozonated water is preferable because it can more uniformly oxidize the particle surface and causes the more uniform formation of carboxy groups than treatment with ozone gas.

The concentration of dissolved ozone in the ozonated water is not particularly limited; however, the lower limit thereof is preferably 20 ppm. A dissolved ozone concentration of less than 20 ppm requires a long time to form a carboxy group, or cannot sufficiently suppress the non-specific adsorption or the like of a substance to be detected since it causes the insufficient formation of a carboxy group. The lower limit of the dissolved ozone concentration is more preferably 50 ppm.

The ozonated water can be prepared, for example by a method involving contacting raw material water with ozone gas via an ozone gas-permeable membrane allowing only gas to pass therethrough and blocking the permeation of liquid as described, for example, in JP 2001-330969 A.

Under alkali conditions, it can be considered that the carboxy groups introduced into the surface of the base material particle are in a nearly dissociated state and produce weak cation exchange interaction with a few cations in a nucleic acid base.

It can also be considered that treatment with ozonated water causes the formation of hydrophilic groups such as a hydroxyl group, an aldehyde group, and a keto group in addition to a carboxy group and the presence of these hydrophilic groups weakens hydrophobic interaction acting between the filler surface and the nucleic acid.

Thus, it can be considered that the use of a filler having strong cationic groups and weak anionic groups on at least the surface improves separation performance by the action of the weak cation exchange interaction and the weakening of the hydrophobic interaction as described above in addition to the anion exchange interaction acting between the filler surface and a nucleic acid as the main interaction.

The amount of the weak anionic groups introduced into at least the surface of the base material particle is not particularly limited provided that it is smaller than or equal to the amount of the strong cationic group.

The base material particle which can be used is, for example, a synthetic polymer fine particle obtained using a polymerizable monomer or the like, and an inorganic fine particle such as silica; however, it is preferably one consisting of a hydrophobic cross-linked polymer particle consisting of an organic synthetic polymer and a layer consisting of a hydrophilic polymer having ion exchange groups copolymerized on the surface of the hydrophobic cross-linked polymer particle.

The hydrophobic cross-linked polymer may be a hydrophobic cross-linked polymer obtained by homopolymerizing one hydrophobic cross-linkable monomer, a hydrophobic cross-linked polymer obtained by copolymerizing two or more hydrophobic cross-linkable monomers, or a hydrophobic cross-linked polymer obtained by copolymerizing at least one hydrophobic cross-linkable monomer and at least one hydrophobic non-cross-linkable monomer.

The hydrophobic cross-linkable monomer is not particularly limited provided that it has 2 or more vinyl groups in one molecule of the monomer. Examples thereof include di(meth)acrylic esters such as ethylene glycol di(meth) acrylate, polyethylene glycol di(meth)acrylate, propylene glycol di(meth)acrylate, and polypropylene glycol di(meth) acrylate; tri(meth)acrylic esters or tetra(meth)acrylic esters such as tetramethylol methane tri(meth)acrylate, trimethylol propane tri(meth)acrylate, and tetramethylol methane tetra (meth)acrylate; and aromatic compounds such as divinylbenzene, divinyltoluene, divinylxylene, and divinylnaphthalene.

As used herein, the "(meth)acrylic" means "acrylic or methacrylic", and the "(meth)acrylate" means "acrylate or methacrylate".

The hydrophobic non-cross-linkable monomer is not particularly limited provided that it is a non-cross-linkable polymerizable organic monomer having hydrophobic properties; examples thereof include (meth)acrylic esters such as methyl(meth)acrylate, ethyl(meth)acrylate, propyl(meth) acrylate, isopropyl(meth)acrylate, butyl(meth)acrylate, and t-butyl(meth)acrylate, and styrene monomers such as styrene and methylstyrene.

When the hydrophobic cross-linked polymer consists of a copolymer of a hydrophobic cross-linkable monomer and a hydrophobic non-cross-linkable monomer, the lower limit of the content of the segment derived from the hydrophobic cross-linkable monomer in the hydrophobic cross-linked polymer is preferably 10% by weight, more preferably 20% by weight.

The hydrophilic polymer having ion exchange groups is composed of a hydrophilic monomer having an ion exchange group and shall contain the segment derived from a hydrophilic monomer having one or more kinds of ion exchange groups. Thus, Methods for producing a hydrophilic polymer having ion exchange groups include a method involving homopolymerizing a hydrophilic monomer having an ion exchange group and a method involving copolymerizing a hydrophilic monomer having an ion exchange group and a hydrophilic monomer not having an ion exchange group.

The hydrophilic monomer having an ion exchange group is preferably one having a strong cationic group and more preferably one having a quaternary ammonium group. Specific examples thereof include ethyl methacrylate trimethylammonium chloride, ethyl methacrylate triethylammonium chloride, ethyl methacrylate dimethylethylammonium chloride, ethyl acrylate trimethylammonium chloride, ethyl acrylate triethylammonium chloride, ethyl acrylate dimethylethylammonium chloride, acrylamide ethyltrimethylammonium chloride, acrylamide ethyltriethylammonium chloride, and acrylamide ethyldimethylethylammonium chloride.

The average particle diameter of the filler is not particularly limited; however, the preferable lower limit thereof is 0.1 μm, and the preferable upper limit is 20 μm. An average particle diameter of the filler of less than 0.1 μm increases the internal pressure of the column and may cause poor separation. An average particle diameter of the filler of more than 20 μm makes dead volume in the column too large and may cause poor separation.

As used herein, the average particle diameter refers to the volume average particle diameter, and can be measured using a particle size distribution analyzer (AccuSizer780 from Particle Sizing Systems).

According to the detection method for single nucleotide polymorphisms of the present invention, the size of the product amplified by the AS-PCR method is preferably 200 bp or less. A size of the product amplified by the AS-PCR method of more than 200 bp may prolong amplification time of PCR and analysis time in ion-exchange chromatography or may cause insufficient separation performance. The size of the product amplified by the AS-PCR method is preferably 100 bp or less.

According to the detection method for single nucleotide polymorphisms of the present invention, the size difference of the products (difference in chain length) between the wild-type and mutant-type amplified by the AS-PCR method is preferably 10 bp or less. When AS primers are designed so that the size difference of the products between the amplified wild-type and mutant-type exceeds 10 bp, desired amplification products may not be obtained due to a non-specific amplification reaction and the like.

Advantageous Effects of Invention

According to the present invention, a method can be provided for rapidly and simply detecting single nucleotide polymorphisms.

DESCRIPTION OF EMBODIMENTS

Figure 1:
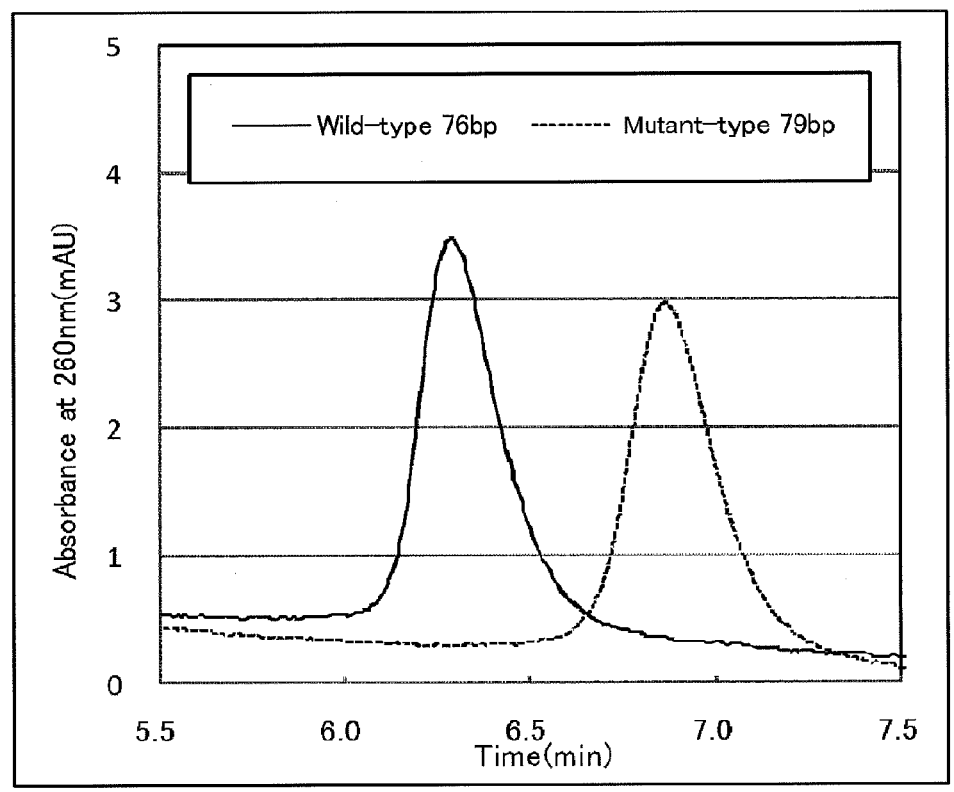
FIG. 1 is a pair of chromatograms obtained by separating and detecting wild-type 76 bp and mutant-type 79 bp in UGT1A1*6 region using anion exchange column 1 in Example 1.

The present invention will be described below in further detail with reference to Examples. However, the present invention is not limited to only these Examples.

(Provision of Anion Exchange Column)
(Anion Exchange Column 1)

In a reactor provided with a stirrer, 300 g of tetraethylene glycol dimethacrylate (from Shin-Nakamura Chemical Co., Ltd.), 100 g of triethylene glycol dimethacrylate (from Shin-Nakamura Chemical Co., Ltd.), and 1.0 g of benzoyl peroxide (from Kishida Chemical Co., Ltd.) were added to 2,000 mL of aqueous solution of 3% by weight polyvinyl alcohol (from Nippon Synthetic Chemical Industry Co., Ltd.). The mixture was heated while stirring and polymerized at 80° C. for 1 hour in an atmosphere of nitrogen. Then, 100 g of ethyl methacrylate trimethylammonium chloride (from Wako Pure Chemical Industries Ltd.) as a monomer having a strong cationic ion exchange group (a quaternary ammonium group) was dissolved in ion-exchange water, and the resultant solution was further added into the reactor. Subsequently, the solution was polymerized at 80° C. for 2 hours in an atmosphere of nitrogen while stirring to provide a polymer composition. The resultant polymer composition was washed with water and acetone to provide hydrophilic coated polymer particles having quaternary ammonium groups on the surface of base material particles.

10 g of the resultant coated polymer particles were immersed in 300 mL of ozonated water having a dissolved ozone concentration of 100 ppm and stirred for 30 minutes. After stirring, centrifugation was performed using a centrifuge ("Himac CR20G" from Hitachi, Ltd.), and the supernatant was removed. This operation was repeated 2 times, and ozonated water treatment was applied to the coated polymer particles to provide a filler for ion-exchange chromatography in which quaternary ammonium groups and carboxy groups coexist.

The ozonated water was prepared using an ozonated water production system in which 400 hollow tube-shaped ozone gas permeable membranes 0.5 mm in inside diameter, 0.04 mm in thickness, and 350 cm in length were enclosed in a cylindrical mantle 15 cm in inside diameter and 20 cm in length (from Sekisui Chemical Co., Ltd.).

When the resultant filler for ion-exchange chromatography was measured using a particle size distribution analyzer ("Accusizer780" from Particle Sizing Systems), the average particle diameter thereof was found to be 10 μm.

The following column (anion exchange column 1) was provided using the resultant filler for ion-exchange chromatography.

Column size: 4.6 mm in inside diameter×20 mm
Ion exchange group: quaternary ammonium group (Anion Exchange Column 2)

The following column as a commercially available column was provided.

Product name: TSK-gel DNA-STAT (from Tosoh Corporation)
Column size: 4.6 mm in inside diameter×100 mm in length
Ion exchange group: quaternary ammonium group Example 1

The separation and detection of wild-type 76 bp and mutant-type 79 bp in UGT1A1*6 region was performed in Example 1.

(AS-PCR Amplification)
Wild-type and mutant-type amplification products were obtained using AS-PCR conditions as described below.

(1) Reagent
AccuPrime Taq DNA Polymerase High Fidelity (from Invitorgen, Lot. 760816)
10×AccuPrime PCR Buffer I
AccuPrime Taq DNA Polymerase High Fidelity (5 U/μL)
UGT1A1*6 primer (from Operon Biotechnologies)

```
Forward (wild-type) (10 pmol/μL):
                                    (SEQ ID NO: 1)
5'-(cgcctcgttgtacatcagagcgg)-3'

Forward (mutant-type) (10 pmol/μL):
                                    (SEQ ID NO: 2)
5'-(ctgacgcctcgttgtacatcagagcga)-3"

Reverse (10 pmol/μL):
                                    (SEQ ID NO: 3)
5'-(cacatcctccctttggaatggca)-3"
```

Nuclease-free Water (not DEPC-treated) (from Ambion, Lot. 0803015)
UGT1A1 gene wild-type sequence-inserted plasmid ($1\times10^6$ copies/μL)
UGT1A1 gene mutant-type sequence-inserted plasmid ($1\times10^6$ copies/μL)

(2) Preparation
One (1) μL of each UGT1A1 gene sequence-inserted plasmid was added to a solution prepared by adding Nuclease-free Water to 5 μL of 10×AccuPrime PCR Buffer I, 1 μL of the Forward primer, and 1 μL of the Reverse primer to make a total volume of 49 μL of a reaction solution.

(3) Reaction
PCR reaction was performed using C1000 (from BIO-RAD Laboratories). The temperature cycle is as described below.

The template was heat-degenerated at 94° C. for 30 seconds; the amplification cycle of 94° C. for 15 seconds, 62° C. for 15 seconds, and 68° C. for 30 seconds was repeated 40 times; and finally, incubation was carried out at 68° C. for 5 minutes. The samples were stored at 4° C. until use.

After AS-PCR amplification, bands derived from the amplification product were identified at about 80 bp by electrophoresis ("Mupid-ex" from Advance Co., Ltd.). The amplification product size was determined using 20 bp DNA Ladder Marker (from Takara Bio Inc.).

(HPLC Analysis)
Using the provided anion exchange column, the AS-PCR amplification products were separated and detected under the following conditions.
System: LC-20A series (from Shimadzu Corporation)
Eluent: eluent A 25 mmol/L Tris-Hydrochloride buffer (pH 7.5)
  eluent B 25 mmol/L Tris-Hydrochloride buffer (pH 7.5)+1 mol/L guanidine hydrochloride
Analysis time: Analysis time was 10 minutes when anion exchange column 1 was used.
  Analysis time was 20 minutes when anion exchange column 2 was used.
Elution method: the mixing ratio of eluent B was linearly increased using the following gradient conditions.
  Conditions when anion exchange column 1 was used
  0 minute (eluent B 40%)→10 minutes (eluent B 50%)
  Conditions when anion exchange column 2 was used
  0 minute (eluent B 70%)→20 minutes (eluent B 90%)
Analyte: Wild-type 76 bp in UGT1A1*6 region
  Mutant-type 79 bp in UGT1A1*6 region
Flow rate: 0.5 mL/min. (when anion exchange column 1 was used)
  1.0 mL/min. (when anion exchange column 2 was used)
Detection wavelength: 260 nm
Sample injection volume: 10 μL

Reference Example 1

The separation and detection of wild-type 271 bp and mutant-type 274 bp in UGT1A1*6 region were performed in Reference Example 1.

(AS-PCR Amplification)

Wild-type and mutant-type amplification products were obtained using the following AS-PCR conditions.

(1) Reagent

AccuPrime Taq DNA Polymerase High Fidelity (from Invitrogen, Lot. 760816)
10×AccuPrime PCR Buffer I
AccuPrime Taq DNA Polymerase High Fidelity (5 U/µL)
UGT1A1*6 primer (from Operon Biotechnologies)

```
Forward (wild-type) (10 pmol/µL):
                                    (SEQ ID NO: 1)
5'-(cgcctcgttgtacatcagagcgg)-3'

Forward (mutant-type) (10 pmol/µL):
                                    (SEQ ID NO: 2)
5'-(ctgacgcctcgttgtacatcagagcga)-3"

Reverse (10 pmol/µL):
                                    (SEQ ID NO: 4)
5'-(gaaagggtccgtcagcatgac)-3"
```

Nuclease-free Water (not DEPC-treated) (from Ambion, Lot. 0803015)
UGT1A1 gene wild-type sequence-inserted plasmid (1×10$^6$ copies/µL)
UGT1A1 gene mutant-type sequence-inserted plasmid (1×10$^6$ copies/µL)

(2) Preparation

One (1) µL of each UGT1A1 gene sequence-inserted plasmid was added to a solution prepared by adding Nuclease-free Water to 5 µL of 10×AccuPrime PCR Buffer I, 1 µL of the Forward primer, and 1 µL of the Reverse primer to make a total volume of 49 µL of a reaction solution.

(3) Reaction

PCR reaction was performed using C1000 (from BIO-RAD Laboratories). The temperature cycle is as described below.

The template was heat-degenerated at 94° C. for 30 seconds; the amplification cycle of 94° C. for 15 seconds, 62° C. for 15 seconds, and 68° C. for 30 seconds was repeated 40 times; and finally, incubation was carried out at 68° C. for 5 minutes. The samples were stored at 4° C. until use.

After AS-PCR amplification, bands derived from the amplification product were identified at about 270 bp (between 200 bp and 300 bp) by electrophoresis ("Mupid-ex" from Advance Co., Ltd.). The amplification product size was determined using 20 bp DNA Ladder Marker (from Takara Bio Inc.).

(HPLC Analysis)

Using the provided anion exchange column, the AS-PCR amplification products were separated and detected under the following conditions.

System: LC-20A series (from Shimadzu Corporation)
Eluent: eluent A 25 mmol/L Tris-Hydrochloride buffer (pH 7.5)
    eluent B 25 mmol/L Tris-Hydrochloride buffer (pH 7.5)+1 mol/L guanidine hydrochloride
Analysis time: Analysis time was 10 minutes when anion exchange column 1 was used.
    Analysis time was 20 minutes when anion exchange column 2 was used.

Elution method: the mixing ratio of eluent B was linearly increased using the following gradient conditions.
    Conditions when anion exchange column 1 was used
      0 minute (eluent B 60%)→10 minutes (eluent B 80%)
    Conditions when anion exchange column 2 was used
      0 minute (eluent B 80%)→20 minutes (eluent B 100%)
Analyte: Wild-type 271 bp in UGT1A1*6 region
    Mutant-type 274 bp in UGT1A1*6 region
Flow rate: 0.5 mL/min. (when anion exchange column 1 was used)
    1.0 mL/min. (when anion exchange column 2 was used)
Detection wavelength: 260 nm
Sample injection volume: 10 µL

Comparative Example 1

The separation and detection of wild-type 76 bp and mutant-type 96 bp in UGT1A1*6 region were attempted to be performed in Comparative Example 1.

(1) Reagent

AccuPrime Taq DNA Polymerase High Fidelity (from Invitorgen, Lot. 760816)
10×AccuPrime PCR Buffer I
AccuPrime Taq DNA Polymerase High Fidelity (5 U/µL)
UGT1A1*6 primer (from Operon Biotechnologies)

```
Forward (wild-type) (10 pmol/µL):
                                    (SEQ ID NO: 1)
5'-(cgcctcgttgtacatcagagcgg)-3'

Forward (mutant-type) (10 pmol/µL):
                                    (SEQ ID NO: 5)
5'-(atagttgtcctagcacctgacgcctcgttgtacatcagagcga)-3"

Reverse (10 pmol/µL):
                                    (SEQ ID NO: 3)
5'-(cacatcctcccttttggaatggca)-3"
```

Nuclease-free Water (not DEPC-treated) (from Ambion, Lot. 0803015)
UGT1A1 gene wild-type sequence-inserted plasmid (1×10$^6$ copies/µL)
UGT1A1 gene mutant-type sequence-inserted plasmid (1×10$^6$ copies/µL)

(2) Preparation

One (1) µL of each UGT1A1 gene sequence-inserted plasmid was added to a solution prepared by adding Nuclease-free Water to 5 µL of 10×AccuPrime PCR Buffer I, 1 µL of the Forward primer, and 1 µL of the Reverse primer to make a total volume of 49 µL of a reaction solution.

(3) Reaction

PCR reaction was performed using C1000 (from BIO-RAD Laboratories). The temperature cycle is as described below.

The template was heat-degenerated at 94° C. for 30 seconds; the amplification cycle of 94° C. for 15 seconds, 62° C. for 15 seconds, and 68° C. for 30 seconds was repeated 40 times; and finally, incubation was carried out at 68° C. for 5 minutes. The samples were stored at 4° C. until use.

When, after AS-PCR amplification, the amplification product was determined by electrophoresis ("Mupid-ex" from Advance Co., Ltd.), many bands likely to indicate non-specific amplification were identified. This means that the AS-PCR amplification was not properly performed. Thus, HPLC analysis was not carried out.

Reference Example 2

The separation and detection of wild-type 76 bp and mutant-type 79 bp in UGT1A1*6 region were performed in Reference Example 2.

HPLC analysis was performed using anion exchange column 2 in the same way as Example 1, except that the salt added to eluent B was sodium chloride in place of guanidine hydrochloride.

Figure 2:
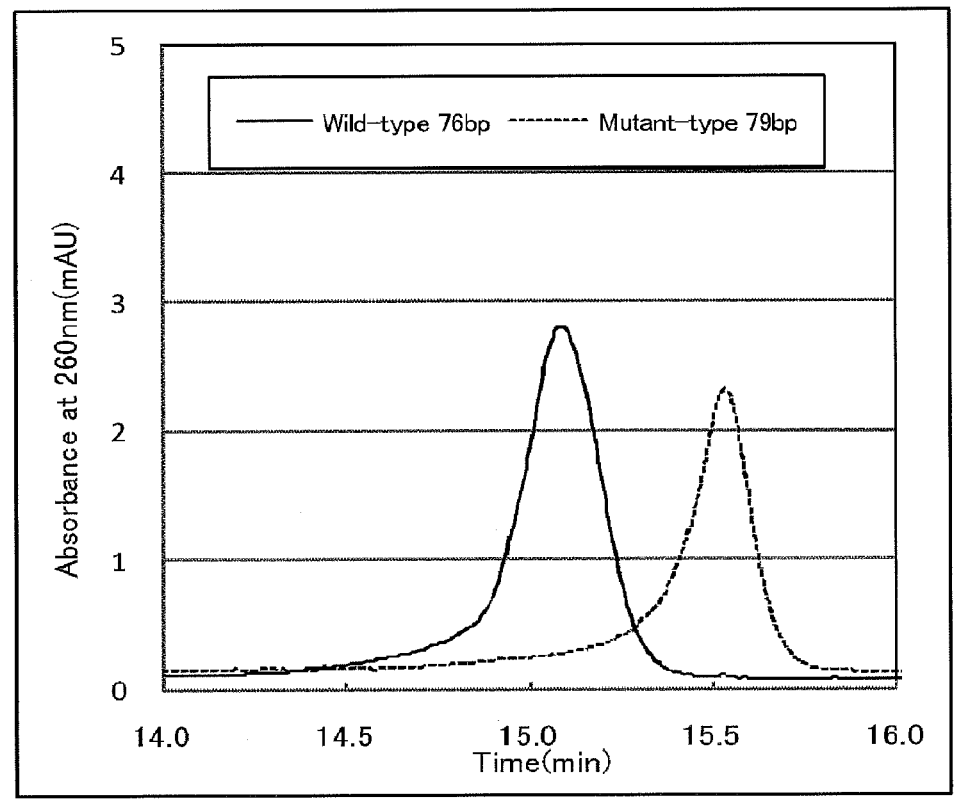
FIG. 2 is a pair of chromatograms obtained by separating and detecting wild-type 76 bp and mutant-type 79 bp in UGT1A1*6 region using anion exchange column 2 in Example 1.

The chromatograms obtained by separating and detecting wild-type 76 bp and mutant-type 79 bp in UGT1A1*6 region in Example 1 are shown in FIG. 1 (when anion exchange column 1 is used) and FIG. 2 (when anion exchange column 2 is used). The results of FIGS. 1 and 2 show that both columns could favorably separate and detect the wild-type 76 bp and mutant-type 79 bp in UGT1A1*6 region amplified by AS-PCR. Particularly, the use of anion exchange column 1 could almost completely separate and detect them in a short time.

Figure 3:
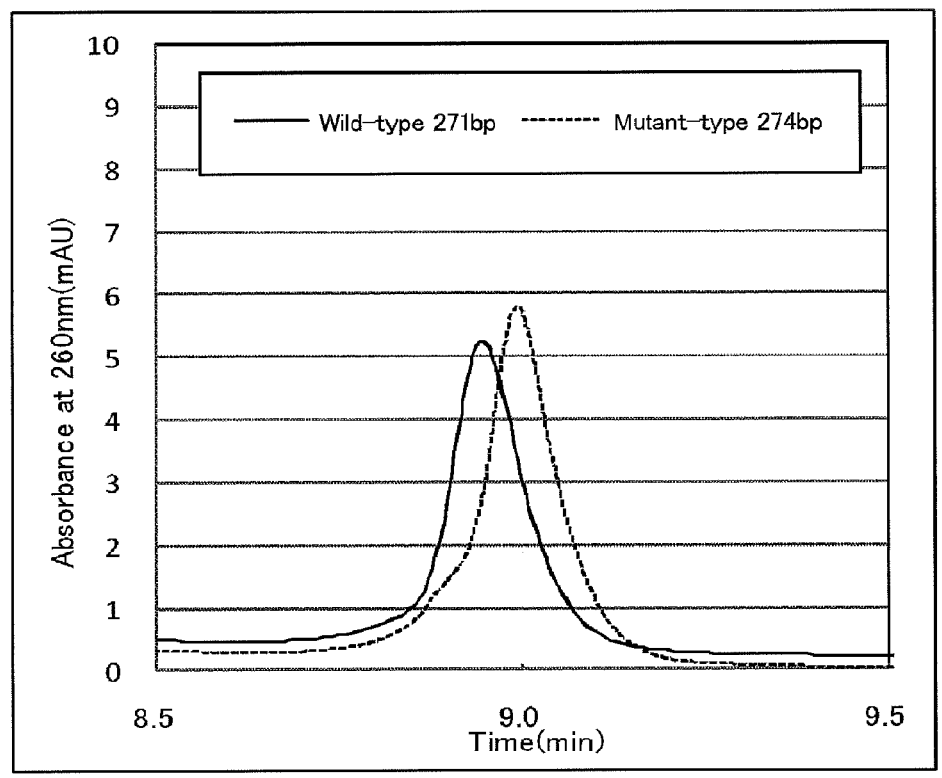
FIG. 3 is a pair of chromatograms obtained by separating and detecting wild-type 271 bp and mutant-type 274 bp in UGT1A1*6 region using anion exchange column 1 in Reference Example 1.
Figure 4:
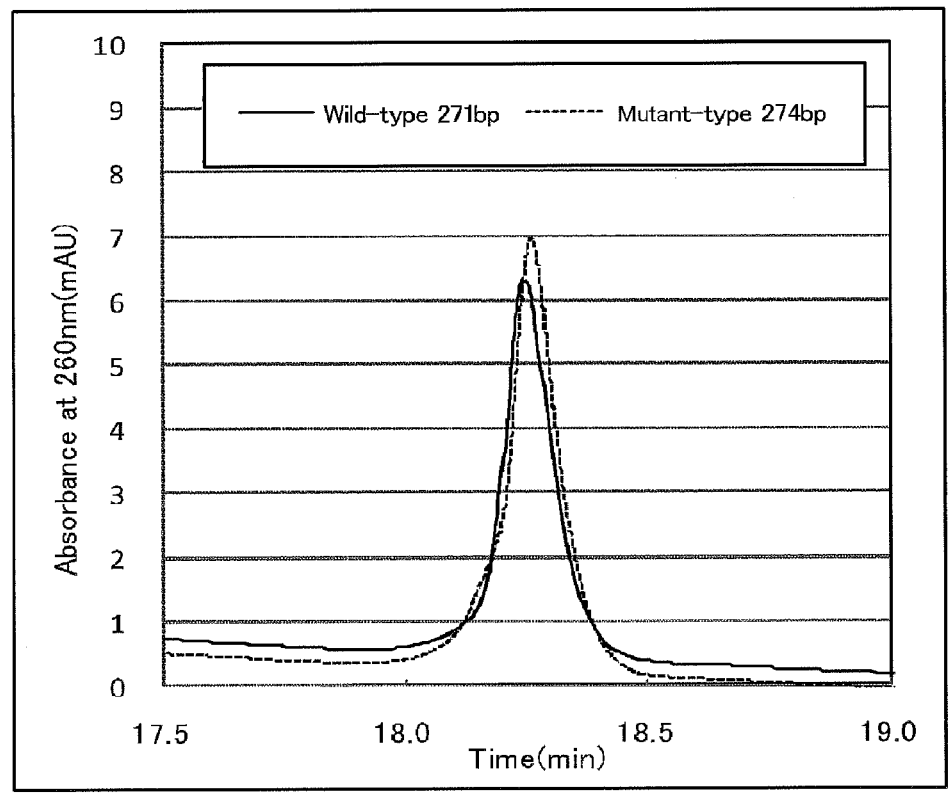
FIG. 4 is a pair of chromatograms obtained by separating and detecting wild-type 271 bp and mutant-type 274 bp in UGT1A1*6 region using anion exchange column 2 in Reference Example 1.

The chromatograms obtained by separating and detecting wild-type 271 bp and mutant-type 274 bp in UGT1A1*6 region in Reference Example 1 are shown in FIG. 3 (when anion exchange column 1 is used) and FIG. 4 (when anion exchange column 2 is used). The results of FIGS. 3 and 4 show that the wild-type 271 bp and mutant-type 274 bp in UGT1A1*6 region amplified by AS-PCR could not be separated in contrast to Example 1. It can be considered that the reason for this lies in the fact that, compared to the size of the AS-PCR amplification products, the difference in the chain length between the wild-type and the mutant-type was relatively small.

Figure 5:
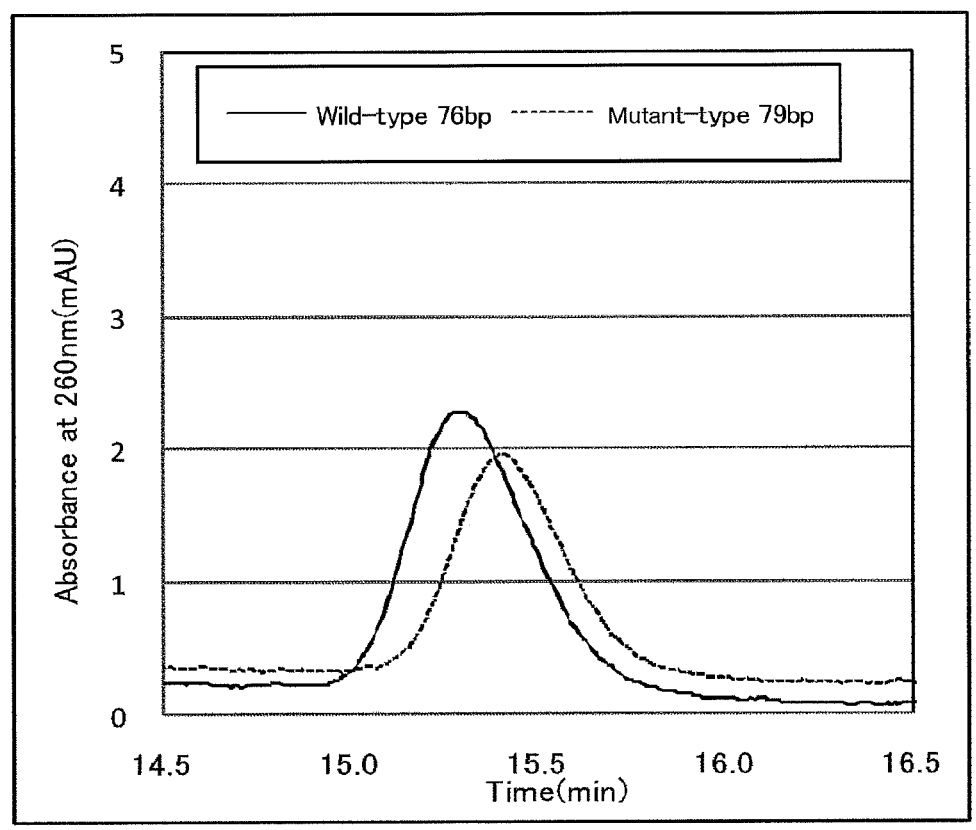
FIG. 5 is a pair of chromatograms obtained by separating and detecting wild-type 76 bp and mutant-type 79 bp in UGT1A1*6 region using anion exchange column 1 in Reference Example 2.

The chromatograms obtained by separating and detecting wild-type 76 bp and mutant-type 79 bp in UGT1A1*6 region in Reference Example 2 are shown in FIG. 5. When sodium chloride was added in place of guanidine hydrochloride to the eluent B, the wild-type 76 bp and the mutant-type 79 bp could not be separated.

INDUSTRIAL APPLICABILITY

According to the present invention, a method can be provided for rapidly and simply detecting single nucleotide polymorphisms.

The invention claimed is:

1. A method for detecting single nucleotide polymorphisms, comprising:
   a step of preparing a reaction solution which comprises a wild-type allele specific primer, a mutant-type allele specific primer, and a template;
   a step of subjecting the reaction solution to PCR amplification and producing PCR amplification products;
   a step of applying the PCR amplification products to an anion exchange column comprising filler having strong cationic groups on at least a surface of base material particles; and
   a step of separating and detecting wild-type and mutant-type products by eluting the PCR amplification products with a guanidine hydrochloride or a guanidine sulfate.

2. The method for detecting single nucleotide polymorphisms according to claim 1, wherein a difference in base pair length between the wild-type allele specific primer and the mutant-type allele specific primer is 1 bp to 10 bp.

* * * * *